United States Patent [19]
Li et al.

[11] Patent Number: 6,084,096
[45] Date of Patent: Jul. 4, 2000

[54] TRIETHYLENEDIAMINE AND PIPERAZINE SYNTHESIS USING ZEOLITE CATALYSTS MODIFIED WITH A SILICON-CONTAINING COMPOUND

[75] Inventors: Hong-Xin Li; Jose Guadalupe Santiesteban, both of Allentown; Lenore Ann Emig, Whitehall; John Nelson Armor, Orefield, all of Pa.

[73] Assignee: Air Products and Chemicals, Inc., Allentown, Pa.

[21] Appl. No.: 09/057,662

[22] Filed: Apr. 9, 1998

[51] Int. Cl.[7] ............... C07D 487/08; C07D 295/027; C07D 295/023; B01J 29/40
[52] U.S. Cl. .................. 544/352; 544/358; 502/71
[58] Field of Search ....................... 544/352, 358

[56] References Cited

U.S. PATENT DOCUMENTS

| | | | |
|---|---|---|---|
| 3,956,329 | 5/1976 | Murakami et al. | 260/268 SY |
| 4,804,758 | 2/1989 | Hoelderich et al. | 544/352 |
| 4,966,969 | 10/1990 | Sato | 544/352 |
| 5,041,548 | 8/1991 | Sato et al. | 544/352 |
| 5,365,004 | 11/1994 | Beck et al. | 585/475 |
| 5,567,666 | 10/1996 | Beck | 502/71 |
| 5,731,449 | 3/1998 | Li | 544/352 |
| 5,741,906 | 4/1998 | Santiesteban | 544/352 |

FOREIGN PATENT DOCUMENTS

| | | |
|---|---|---|
| 0158319 | of 0000 | European Pat. Off. . |
| 0312734 | of 0000 | European Pat. Off. . |
| 0313753 | of 0000 | European Pat. Off. . |
| 0593086 | of 0000 | European Pat. Off. . |
| 0382055 | of 0000 | Germany . |
| 0423526 | of 0000 | Germany . |

OTHER PUBLICATIONS

Reichle Journal of Catalysis (vol. 144, p 556–568, 1983).

*Primary Examiner*—Mark L. Berch
*Attorney, Agent, or Firm*—Michael Leach

[57] ABSTRACT

A process for preparing triethylenediamine and piperazine by passing an ethanolamine, ethyleneamine, piperazine or morpholine over a pentasil-type zeolite at elevated temperature characterized by employing a ZSM-5 zeolite in the hydrogen or ammonium form which has been treated with a passivating agent which is a silicon-containing compound capable of deactivating the acidic sites on the zeolite surface.

18 Claims, No Drawings

TRIETHYLENEDIAMINE AND PIPERAZINE SYNTHESIS USING ZEOLITE CATALYSTS MODIFIED WITH A SILICON-CONTAINING COMPOUND

BACKGROUND OF THE INVENTION

The present invention relates to the preparation of triethylenediamine (TEDA) and piperazine (PIP) by contacting nitrogen-containing compounds with zeolites at elevated temperature.

The synthesis of TEDA and PIP from a variety of amine compounds using metallosilicates is well known in the art.

U.S. Pat. No. 3,956,329 discloses a process for preparing TEDA from a number of amine compounds using untreated zeolite catalysts with a $SiO_2/Al_2O_3$ (silica to alumina) ratio between 2 and 12.

U.S. Pat. No. 4,804,758 discloses the preparation of TEDA from certain heterocyclic amines in the presence of borosilicate and/or iron silicate zeolites as catalysts.

U.S. Pat. No. 4,966,969 and 5,041,548 disclose the preparation of TEDA from amine compounds using a catalyst comprising a crystalline metallosilicate having a silica/metal oxide molar ratio of 12/1 or more, in particular, a metallosilicate crystallized in the presence of an organic crystallizing agent.

EP 158 319 discloses a method of preparing TEDA by contacting acyclic or heterocyclic amines with untreated high-silica zeolite having a silica to alumina ratio of at least 20 to 1.

EP 382 055 discloses a process for synthesizing TEDA from ethylenediamine and 0 to 200 mole % PIP on aluminum, boron, gallium and/or iron silicate zeolites.

EP 423 526 discloses the preparation of TEDA and PIP from ethylenediamine-water mixtures which is catalyzed by zeolites of the pentasil type with weakened acidity, i.e., which contain alkali metal ions or in which the aluminum of the zeolite skeleton has been isomorphously replaced by iron.

EP 312 734 discloses that PIP can be converted directly to TEDA in the presence of untreated zeolites having a pentasil, especially a ZSM-5, structure.

EP 313 753 discloses the preparation of mixtures of TEDA and PIP from polyethylene polyamines and/or ethanolamines using an untreated pentasil zeolite.

Journal of Catalysis (vol. 144, p556–568, 1993) describes the use of pentasil type zeolites for TEDA synthesis from a variety of polyamines.

Selectivation of zeolites with silicon compounds has been used for improving catalytic properties of some specific processes:

U.S. Pat. No. 5,365,004 discloses zeolite catalysts which have been modified by being ex situ selectivated with a silicon compound to improve their catalytic properties for hydrocarbon conversions such as toluene disproportionation process.

EP 593, 086 discloses treatment of mordenite zeolite with tetraethyl orthosilicate (TEOS) to improve the selectivity for methylamine synthesis.

BRIEF SUMMARY OF THE INVENTION

The present invention is directed to a process for preparing TEDA and PIP by contacting an amine-containing compound with a pentasil-type zeolite in the hydrogen (H+) and/or ammonium ($NH_4+$) form at elevated temperatures. The zeolite catalyst used in the process is one whose surface has been at least partially passivated prior to or after its conversion to the H+ or $NH_4+$ form. Passivation is performed by treating the zeolite with certain silicon compounds in an organic solvent.

Such surface passivation treatment at least partially and permanently deactivates, or selectivates, the external sites of the zeolite catalyst for acid catalyzed reactions by providing a coating of silicon material on the surface and surprisingly improves the selectivity toward TEDA and PIP production. Some of the amine compounds typically used in making TEDA and PIP, such as etyhylenediamine (EDA) are very reactive on the external sites of untreated zeolite catalysts giving undesired products.

DETAILED DESCRIPTION OF THE INVENTION

As the starting material to be used in the process for preparing TEDA and PIP, any amine compounds typically used in the art can be used, such as ethanolamines, including monoethanolamine, diethanolamine and triethanolamine; ethyleneamines, including ethylenediamine, diethylenetriamine and triethylenetetramine; piperazines including piperazine, N-hydroxyethylpiperazine, bis-(hydroxyethyl) piperazine and N-aminoethylpiperazine; morpholine and obviously mixtures of the foregoing.

The crystalline metallosilicate (zeolite), which is used as the catalyst in the process, has a crystal skeleton mainly comprised of silicon dioxide (silica; $SiO_2$) and a metal oxide such as aluminum oxide (alumina; $Al_2O_3$), iron oxide or boron oxide. Alumina is the preferred metal oxide. The silica/metal oxide molar ratio is 12:1 or more, preferably 20:1 to 1000:1, and more preferably 50:1 to 500:1. If the silica/metal oxide molar ratio is less than 12:1, the yield of TEDA and PIP may be undesirably low.

There are no special limitations to the crystalline metallosilicate that is used as long as it satisfies the above silica/metal oxide molar ratio. Crystalline aluminosilicates having a main pore made of a ten-member ring of oxygen, especially those belonging to members of the pentasil-type structure, are preferred with ZSM-5 zeolite being most preferred.

The preparation of suitable pentasil zeolite catalysts is well known to those skilled in the art as illustrated by the previously cited patents and literature references. In addition, suitable pentasil zeolites are commercially available from many sources such as Degussa AG and CU Chemie Uetikon AG.

Crystalline aluminosilicates of the pentasil family as obtained by hydrothermal synthesis using an organic crystallizing agent are particularly preferred. Among the pentasil types, the zeolite structures ZSM-5, ZSM-11, ZSM-8, and ZSM-5/ZSM-11-intermediates are preferred, especially ZSM-5.

The zeolite catalysts are used in their hydrogen form (H+) and/or their ammonium form ($NH_4+$) after having undergone the surface passivation treatment.

For example, a pentasil-type crystalline aluminosilicate can be prepared by the hydrothermal synthesis using a mixture composed mainly of a silica source, e.g., colloidal silica, silica gel, or silicic acid salts such as water glass, and an aluminum oxide source, e.g., the sulfuric acid salts, nitric acid salts or oxy acid salts of alumina, such as aluminum sulfate and sodium aluminate, in the absence or preferably in the presence of an organic crystallizing agent, e.g., amines such as tetraalkylammonium halide having 2 to 5 carbon atoms.

There is also known a method in which the hydrothermal synthesis is performed in the presence of alkali metal compounds such as the hydroxides and halides of alkali metal such as sodium and the like.

The crystalline aluminosilicate obtained by these methods is generally not of the H+ or $NH_4+$ form, but of the form that H+ and $NH_4+$ are replaced by quaternary ammonium ion and/or alkali metal ion such as Na+ and the like. Therefore, the crystalline aluminosilicate must be changed into the H+ or $NH_4+$ form, and this exchange can be easily achieved by known methods.

With regard to the surface passivation treatment, useful passivating agents, i.e., silicon-containing materials capable of passivating the surface of a crystalline aluminosilicate, include those silicon-containing materials which are disclosed as selectivating agents in U.S. Pat. No. 5,365,004 at Col 5/26–6/16, which disclosure is incorporated by reference.

Examples of silicon-containing passivating agents for use in the passivation treatment include tetraalkoxysilanes, also known as tetraalkyl orthosilicates, such as tetramethoxysilane and tetraethoxysilane, dimer to hexamer of tetraalkoxysilanes, silicon tetrachloride, dimethyldichlorosilane, trimethylchlorosilane, tetramethyldisilazane and hexamethyidisilazane.

The passivating treatment of the zeolite is carried out in a liquid phase. The passivating agent may be directly used, but in general, it is first dissolved in a suitable solvent. Examples of solvents which are often used include aliphatic and alicyclic hydrocarbons such as hexane, octane and cyclohexane, aromatic hydrocarbons such as benzene, toluene and xylene, ethers such as ethyl ether and isopropyl ether, lower alcohols such as methanol, ethanol and isopropyl alcohol, and alkyl ethers of ethylene glycol such as ethylene glycol monomethyl ether and ethylene glycol monoethyl ether.

The desirable solvents are preferably selected in compliance with the kind of passivating agent to be used. The concentration of the passivating agent in the solvent is in the range of from 2 to 30 wt %.

The passivating agent is dissolved in the solvent to form a passivating agent solution, and the aluminosilicate is then suspended in the passivating agent solution to carry out the passivation treatment for the aluminosilicate, whereby a silicon compound is deposited and fixed on the surface of the aluminosilicate.

The temperature at which the passivation treatment is carried out is in the range of from room temperature to the boiling point of the solution and temperatures in the range from 0 to 200° C. are often used. When the treatment is performed under the application of pressure, the treatment temperature can be further raised.

The duration of the passivation treatment depends the treatment temperature, but a treatment time of from 6 to 100 hours is often used with a treatment temperature in the vicinity of room temperature and a time of about 0.5 to 20 hours is often used with a temperature of from 40 to 90° C.

After completion of the passivation treatment, the aluminosilicate is separated from the treatment solution in the usual manner such as filtration or centrifugation, and then heated under an atmosphere of inert gas such as nitrogen or under reduced pressure to remove the adhered or adsorbed organic solvent. Next the aluminosilicate is heated at 300 to 600° C. in an atmosphere of air or oxygen to yield the desired catalyst.

The passivation treatment of the aluminosilicate with the passivation agent is not limited to one operation but it may be repeated a number of times. In particular, the passivation treatment may be repeated several times to afford a catalyst possessing the desired selectivity.

As to the preferred embodiments, the prepared aluminosilicate is contacted, for example, with a 0.01 to 5 molar organic solution of a silicon-containing passivating agent at 0 to 100° C. for sufficient time to effect partial or total surface passivation, e.g., 0.01 to 100 hours, preferably with a 0.03 to 3 molar silicon-containing passivating agent solution at 40 to 90° C. for 0.5 to 20 hours. Preferred passivating agents include such materials as tetraalkyl orthosilicates like tetraethyl orthosilicate (TEOS); silica gels such as those marketed under the trademarks, Hi-Sil, Ultrasil and Ludox; alkylamine silanes such as n-propylamine silane, available as Hydrosil 2627, or polysiloxanes. It is desirable to perform such contact using 5 to 100 mL alcoholic solution/g zeolite, especially using TEOS in ethanol.

The treatment with passivating agent is believed to provide a silicone dioxide coating on the acidic sites of the aluminosilicate surface. The passivation treatment can be combined with other conventional techniques, such as steaming and chemical treatment with inorganic compounds.

For changing the alkali metal ion of the zeolite into H+ or $NH_4+$ prior to passivation, there is often employed a method in which the alkali metal salt-type crystalline aluminosilicate is treated with an aqueous solution of ammonium salts, such as ammonium nitrate and ammonium sulfate, to form an ammonium salt-type crystalline aluminosilicate. The ammonium salt-type crystalline aluminosilicate may then be calcined in the air at a temperature of 300 to 600° C., preferably 400 to 500° C., to obtain the H+ form crystalline zeolite.

While the zeolite as used in the present invention is preferably of the H+ and/or $NH_4+$ form, the H+ and/or $NH_4+$ may be partially replaced by other cations, such as alkali, alkaline earth, rare earth, transition metals, oxides etc., as long as the object of the present invention can be obtained.

The catalyst of the present invention can be used in any desired form, such as powder, particles, strips, spheres and pellets. The catalyst can be self-bound or molded with a binder such as silica, titania and/or zirconia. If alumina, natural clays and/or mixtures of these materials are to be mixed with the zeolite, the zeolite should be first treated with the passivating agent. Naturally occurring clays which can be composited with the zeolite catalyst include the montmorillonite and kaolin families. These clays can be used in the raw state as originally mined or initially subjected to calcination, acid treatment or chemical modification.

Of all the matrix materials mentioned above, materials of low acidity such as silica or zirconia are preferred in that they prevent the unwanted side reactions which are engendered by more active materials such as alumina. The performance of alumina can, however, be improved by altering its acid properties via chemical modification.

The relative proportions of zeolite and matrix material can vary widely with the zeolite content ranging from 10 to 98 wt %, and more usually in the range of 50 to 90 wt %, of the composite.

In accordance with the process of the present invention, the desired TEDA and PIP can be efficiently obtained by reacting amine compounds as the starting material using the described zeolite catalyst under pressures ranging from 0.001 to 200 atm (0.1 to 20,000 kPa), preferably 0.01 to 10 atm (1 to 1000 kPa).

The reaction of the amine compound proceeds on contacting it with the described zeolite catalyst under the above-specified pressure. Reaction conditions, such as reaction temperature, reaction time and starting materials/catalyst ratio, cannot be determined unconditionally because they vary with the type of amine compound, the type of zeolite catalyst, reaction pressure and the like. Usually the reaction temperature is chosen within the range 100 to 450° C., preferably 300 to 400° C.

The reaction can be performed batch-wise, semi-continuously or continuously. In the case of the continuous reaction, WHSV (weight hourly space velocity) is not critical, but usually ranges from 0.01 to 10 $hr^{-1}$. The preferred WHSV is determined depending on the temperature. For example, at 300° C., WHSV is 0.02 to 2 $hr^{-1}$, and at 350° C., it is 0.1 to 5 $hr^{-1}$.

In the reaction of the amine compound as a starting material, it may be diluted with an inert gas such as hydrogen, nitrogen, steam or hydrocarbons, or with an inert solvent such as water and inert hydrocarbons. By using these diluents, the reaction can be controlled appropriately.

EXAMPLES 1 and 2

Examples 1 and 2 compare the results obtained for TEDA and PIP synthesis from an aqueous solution containing 25 wt % ethylenediamine (EDA) using ZSM-5 catalysts before and after treatment with the silicon-containing compound, tetraethyl orthosilicate (TEOS). The operating conditions were: 340° C., 1 atm, and $WHSV_{(EDA)}=1.65$ $h^{-1}$.

In Example 1, HZSM-5 catalyst having a crystal size of ~0.07 micron and a silica/alumina ratio of 90 was used for the reaction. In Example 2, the HZSM-5 catalyst used in Example 1 (10 g) was stirred in a 100 ml ethanolic solution containing 0.7 g TEOS at room temperature for 20 hours. The TEOS treated catalyst was calcined at 500° C. in a flow of air for 4 hours prior to the reaction test. Results in Table 1 show the selectivity for the desired products (TEDA and PIP) increased upon treatment of the catalyst with TEOS.

TABLE 1

| Example | EDA Conversion (%) | TEDA & PIP Selectivity (mole %) |
|---------|--------------------|----------------------------------|
| 1 | 98 | 81 |
| 2 | 95 | 89 |

The data in Table 1 clearly show the beneficial effect of TEDA and PIP selectivity upon treating ZSM-5 zeolite with tetraethyl orthosilicate.

INDUSTRIAL APPLICATION

The present invention provides an improvement in the production of TEDA and PIP from amine compounds using a zeolite catalyst passivated with a silicon-containing compound.

We claim:

1. In a process for preparing triethylenediamine and piperazine by passing an amine compound over a pentasil-type zeolite at elevated temperature, the amine compound being an ethanolamine, an ethyleneamine, a piperazine, morpholine or a mixture of the foregoing, the improvement which comprises employing a pentasil-type zeolite in the hydrogen or ammonium form which has been treated with a surface passivating agent which is a silicon-containing compound that at least partially and permanently deactivates the external sites of the zeolite catalyst for acid catalyzed reactions thereby improving the selectivity toward triethylenediamine and piperazine production.

2. The process of claim 1 in which the passivating agent is a tetraalkyl orthosilicate.

3. The process of claim 2 in which the passivating agent is tetraethyl orthosilicate.

4. The process of claim 1 in which the passivating agent is a silica gel.

5. The process of claim 1 in which the passivating agent is a polysiloxane.

6. The process of claim 2 in which the zeolite has a silica/metal oxide molar ratio of 20:1 to 1000:1.

7. The process of claim 6 in which the zeolite is a ZSM-5, ZSM-8 or ZSM-11 zeolite.

8. The process of claim 7 in which the amine compound is monoethanolamine, diethanolamine, triethanolamine, ethylenediamine, diethylenetriamine, triethylenetetramine, piperazine, N-hydroxyethylpiperazine, bis-(hydroxyethyl) piperazine, N-aminoethylpiperazine, morpholine or a mixture of any of the foregoing.

9. In a process for preparing triethylenediamine and piperazine by passing an amine compound which is an ethanolamine, an ethyleneamine, a piperazine or morpholine, over a pentasil-type zeolite at elevated temperature, the improvement which comprises employing a ZSM-5 zeolite in the hydrogen or ammonium form which has been treated with a passivating agent which is a silicon-containing compound that at least partially and permanently deactivates the external sites of the zeolite catalyst for acid catalyzed reactions thereby improving the selectivity toward triethylenediamine and piperazine production.

10. The process of claim 9 in which the amine compound is ethylenediamine, diethylenetriamine or triethylenetetramine or a mixture thereof.

11. The process of claim 10 in which the zeolite has a silica/alumina molar ratio of 20:1 to 1000:1.

12. The process of claim 11 in which the amine compound is ethylenediamine.

13. The process of claim 12 in which the passivating agent is a tetraalkyl orthosilicate.

14. The process of claim 13 in which the passivating agent is tetraethyl orthosilicate.

15. In a process for preparing triethylenediamine and piperazine by passing an ethyleneamine over a pentasil-type zeolite at elevated temperature, the improvement which comprises employing a ZSM-5 zeolite having a silica/alumina molar ratio of 20:1 to 1000:1 in the hydrogen or ammonium form which has been treated with a 0.01 to 5 molar alcoholic solution of a tetraalkyl orthosilicate.

16. The process of claim 15 in which the zeolite has a silica/alumina molar ratio of 50:1 to 500:1.

17. The process of claim 16 in which the passivating agent is tetraethyl orthosilicate.

18. The process of claim 17 in which the zeolite is treated with 0.03 to 3 molar ethanolic tetraethyl orthosilicate solution.

* * * * *